United States Patent [19]

Osborne

[11] Patent Number: 4,586,926
[45] Date of Patent: May 6, 1986

[54] PERCUTANEOUS ENTRY NEEDLE

[75] Inventor: Thomas A. Osborne, Bloomington, Ind.

[73] Assignee: Cook, Incorporated, Bloomington, Ind.

[21] Appl. No.: 585,950

[22] Filed: Mar. 5, 1984

[51] Int. Cl.⁴ ............................................. A61M 27/00
[52] U.S. Cl. ................................. 604/272; 128/329 R; 604/280
[58] Field of Search ................................ 604/272–274, 604/263, 177, 280; 128/329, 339

[56] References Cited

U.S. PATENT DOCUMENTS

| | | | |
|---|---|---|---|
| 2,638,897 | 5/1953 | Poitras | 604/272 |
| 2,725,058 | 11/1955 | Rathkey | 604/177 |
| 3,074,159 | 1/1963 | Baldwin et al. | 604/272 X |
| 3,090,384 | 5/1963 | Baldwin et al. | 604/272 |
| 3,769,975 | 11/1973 | Nimoy et al. | 604/177 X |
| 4,326,519 | 4/1982 | D'Alto | 604/177 X |
| 4,368,738 | 1/1983 | Tersteegen et al. | 604/272 X |

Primary Examiner—Stephen C. Pellegrino
Attorney, Agent, or Firm—Weikart, Emhardt & Naughton

[57] ABSTRACT

A percutaneous entry needle for use in digital subtraction angiography procedures. The needle includes tubing having one end sharpened for percutaneous entry by a bevel that is at an acute angle to the axis of the tubing. The tubing has a sharp tip defined by the bevel which tip is located on one side of the tubing. A hub is rigidly secured to the other end of the tubing and includes oppositely projecting luer lock ears which project radially from the axis in directions which are at 90° to the position of the sharp tip relative to the axis. There is also provided a rigid flange rigidly secured to the hub and extending radially thereof. The flange is located on the side of the tubing away from the sharp tip and is appropriately sized for gripping by the user.

1 Claim, 6 Drawing Figures

PERCUTANEOUS ENTRY NEEDLE

BACKGROUND OF THE INVENTION

1. Field of the Invention

The present invention is related generally to percutaneous entry needles and more particularly to a needle particularly adapted for use in digital subtraction angiography procedures.

2. Description of the Prior Art

In digital subtraction angiography (DSA) the radiologist can make angiograms without the need to selectively place a catheter. The X-ray contrast opaque liquid is injected into the cardiovascular system anywhere that is convenient and relatively safe. Typically, the radiologist might use a vessel in the arm similar to an IV injection site. However, unlike an IV, where the infusion is made through a needle, the needle is replaced by the Seldinger technique with a small bore short catheter. The contrast material is then injected into the vein through this catheter.

The Seldinger technique involves the use of a wire guide such as the one illustrated in Cook U.S. Pat. No. 3,547,103, and also involves a needle and a catheter. The needle is inserted through the skin into the blood vessel. The coil spring wire guide is then threaded through the lumen of the needle into the blood vessel. The needle is then removed from the blood vessel by moving it over the wire guide and unthreading it from the wire guide while holding the wire guide in position in the blood vessel. The catheter is then threaded onto the wire guide and moved into the blood vessel over the wire guide. The wire guide is then removed from the catheter and the blood vessel leaving the catheter in the blood vessel.

The current needle design commonly used for IV infusions and DSA procedures is a long bevelled needle with two flexible wings attached to the proximal end of the needle. Also attached to the proximal end of the needle is flexible tubing with a luer lock provided at the distal end thereof for coupling to the IV supply. The operator uses such a needle, commonly referred to as a butterfly needle, by folding the wings together on one side giving the operator a means to grasp and insert the needle. When used for an IV, the wings are unfolded and then taped or sutured to the skin to secure the needle in place for the duration of the infusion. When used for DSA, however, the needle is not left in place. It is used to introduce the wire guide and then is removed from the blood vessel. Thus, the wings are not even unfolded.

SUMMARY OF THE INVENTION

One embodiment of this invention might involve a percutaneous entry needle including tubing, having one end sharpened for percutaneous entry by a bevel that is at an acute angle to the axis of the tubing. The tubing has a sharp tip defined by the bevel which tip is located on one side of the tubing. A hub is rigidly secured to the other end of the tubing and includes oppositely projecting luer lock ears which project radially from the axis in directions which are at 90° to the position of the sharp tip relative to the axis. There is also provided a rigid flange rigidly secured to the hub and extending radially thereof. The flange is located on the side of the tubing away from the sharp tip and is appropriately sized for gripping by the user.

It is an object of the invention to provide an improved percutaneous needle. Another object of the invention is to provide a percutaneous needle particularly adapted for DSA procedures. Still another object of the invention is to provide a percutaneous entry needle which is easier to manipulate into a blood vessel.

Related objects and advantages will become apparent as the description proceeds.

DESCRIPTION OF THE PREFERRED EMBODIMENT

Figure 1:
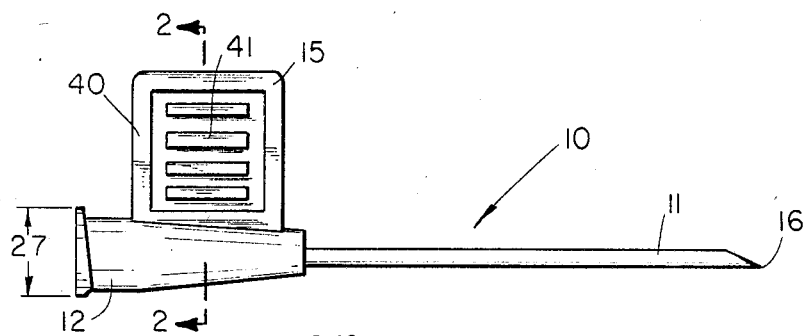
FIG. 1 is a side elevation of the needle of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 3:
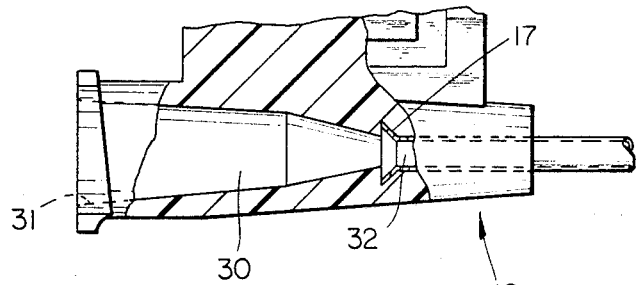
FIG. 3 is a sectional view taken along the line 3—3 of FIG. 2 in the direction of the arrows.
Figure 5:
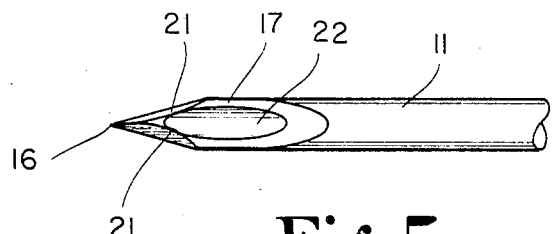
FIG. 5 is an enlarged top plan view of the needle point.
Figure 6:
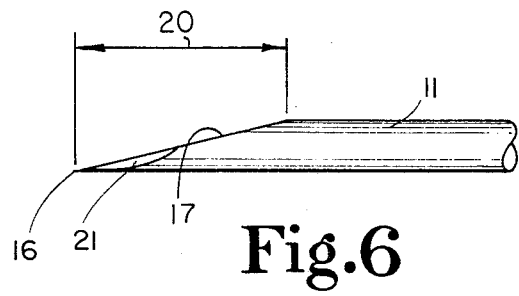
FIG. 6 is a side elevation of the structure shown in FIG. 5.

Referring now to the drawings, there is illustrated a percutaneous entry needle 10 which includes tubing 11, a hub 12, and a flange 15. In one specific embodiment of the invention, the tubing 11 is 18 gauge and has an approximate length of 3.2 cm, this length being measured from the exterior of hub 12 to the tip 16 of the needle. As shown in FIG. 3, the tubing 11 is flared at 17 and the hub 12 is molded about the tubing thus fixing the tubing in the hub 12.

The tubing 11 has one end sharpened for percutaneous entry by bevel 17 which has an approximate length 20 in one embodiment of the invention of 0.5 cm. This relatively long bevel 17 produces a very sharp acute angle with the axis of the tubing and produces a very sharp point on the needle at the tip 16. The needle additionally includes side bevels 21 which further sharpen the tip of the needle.

The long bevel 17 is particularly adapted for use in the digital subtraction angiography needle because the needle is inserted into the blood vessel with the axis of the tubing at a small acute angle relative to the axis of the blood vessel. Because of the fact that the needle when inserted percutaneously into the blood vessel extends generally longitudinally of the blood vessel, the fact that the bevel is long does not provide a situation wherein the lumen 22 is exterior to the blood vessel.

The hub 12 has a luer lock component 25 formed thereon with oppositely projecting ears 26. The luer lock component 25 is adapted for coupling to a standard female luer lock component for connecting the needle to IV fluid or the like. The hub 12 has a relatively small diameter so that its dimension 27 in the above mentioned specific embodiment of the invention is 0.7 cm.

Thus, the percutaneous entry needle can be used while positioned very closely to the skin and blood vessel being entered with the axis of the tubing 11 at a very small acute angle relative to the blood vessel. For this same reason, the oppositely projecting luer lock ears 26 are arranged at 90° to the location of the tip 16 of the needle. The inside of the hub 12 and the tubing 11 is particularly designed to accomodate and guide a wire guide without providing any surfaces upon which the wire guide might hang up when it is moved through the hub and tubing. Thus, the hub 12 has a tapered passageway 30 which extends from the mouth 31 to alignment with the lumen 32 of the tubing 11. The mouth 31 is substantially larger in diameter than the lumen of the tubing.

Figure 2:
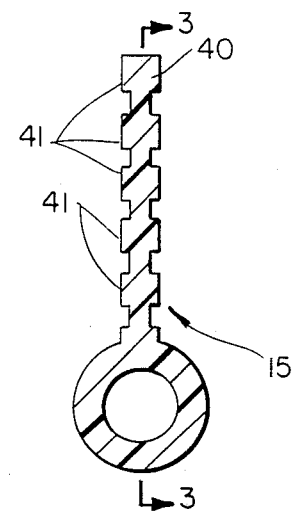
FIG. 2 is an enlarged sectional view taken along the line 2—2 of FIG. 1 in the direction of the arrows.
Figure 4:
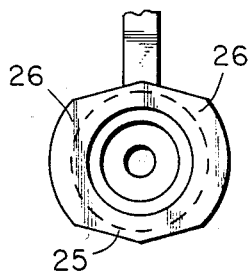
FIG. 4 is an end elevation.

The flange 15 includes a rib 40 which extends entirely around the flange and along with a series of parallel ribs 41 provides means increasing the rigidity of the flange 15. As illustrated in FIG. 2, the flange 15 is formed integrally with the hub 12. The flange 15 provides secure means for grasping the percutaneous entry needle when it is used for entry into a blood vessel.

It will be evident from the above description that the present invention provides an improved percutaneous needle which is particularly adapted for DSA procedures. The design of the needle makes it easy to grasp the needle and to position it with the hub relatively close to the skin and with the tubing 11 at an almost parallel very small acute angle relationship with the blood vessel. The relatively sharp tip provided by the long bevel 17 also facilitates entry of the needle into the blood vessel. The design of the needle also permits convenient use of a wire guide as well as provides for connection to the luer lock of an IV.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed:

1. A percutaneous entry needle comprising:
   tubing having one end sharpened for percutanious entry by a bevel that is at an acute angle to the axis of the tubing, said tubing having a sharp tip defined by said bevel which sharp tip is located on one side of said tubing, said tubing having an outer diameter of approximately 18 gauge and the length of said bevel being approximately 0.5 cm.;
   a hub rigidly secured to the other end of said tubing, said hub including oppositely projecting luer lock ears which project radially from said axis in directions which are at ninety degrees (90°) to the position of said sharp tip relative to said axis, said hub having a passageway therein that is aligned with said tubing, said hub passageway having a mouth which is larger in diameter than the lumen of said tubing, said passageway tapering inside from said mouth to a smaller size at said tubing, which smaller size corresponds to the size of the lumen of said tubing, said tapering passageway being shaped to guide a wire guide into said tubing lumen; and
   a rigid flange rigidly secured to said hub and extending radially thereof, said flange being located on the side of said tubing away from said sharp tip, said rigid flange having ribs, one of said ribs extending around the border of said flange, the rest of said ribs being parallel to one another and located inside of said one rib.

* * * * *